US011980424B1

(12) United States Patent
Thomas et al.

(10) Patent No.: US 11,980,424 B1
(45) Date of Patent: *May 14, 2024

(54) USE OF REAL-TIME AND STORABLE IMAGE DATA STREAM FOR GENERATION OF AN IMMERSIVE VIRTUAL UNIVERSE IN METAVERSE OR A 3-D HOLOGRAM, FOR MEDICAL AND VETERINARY TEACHING AND TRAINING

(71) Applicant: Mammen Thomas, Seattle, WA (US)

(72) Inventors: Mammen Thomas, Seattle, WA (US); Arun Mammen Thomas, Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/384,864

(22) Filed: Oct. 29, 2023

Related U.S. Application Data

(63) Continuation of application No. 17/974,538, filed on Oct. 27, 2022, now Pat. No. 11,850,005.

(51) Int. Cl.

| | | |
|---|---|---|
| *G03H 1/22* | (2006.01) | |
| *A61B 34/10* | (2016.01) | |
| *A61B 90/00* | (2016.01) | |
| *G02B 27/09* | (2006.01) | |
| *G06T 7/33* | (2017.01) | |
| *G06T 19/20* | (2011.01) | |
| *G16H 30/40* | (2018.01) | |
| *G16H 40/67* | (2018.01) | |

(Continued)

(52) U.S. Cl.
CPC .............. *A61B 34/10* (2016.02); *A61B 90/37* (2016.02); *G06T 7/344* (2017.01); *G06T 19/20* (2013.01); *G16H 30/40* (2018.01); *G16H 40/67* (2018.01); *A61B 2034/102* (2016.02); *A61B 2034/105* (2016.02); *A61B 2034/2065* (2016.02); *A61B 34/30* (2016.02); *A61B 2090/367* (2016.02); *A61D 1/00* (2013.01); *G06T 2207/20016* (2013.01); *G06T 2210/41* (2013.01); *G06T 2219/024* (2013.01); *G06T 2219/2004* (2013.01)

(58) Field of Classification Search
CPC ... A61B 34/10; A61B 90/37; A61B 2034/102; A61B 2034/2065; G06T 7/344; G06T 19/20
USPC .......................................................... 345/419
See application file for complete search history.

(56) References Cited

U.S. PATENT DOCUMENTS 11,273,003 B1 * 3/2022 Haider ............... G02B 27/0093
11,850,005 B1 * 12/2023 Thomas ................... G06T 19/20
(Continued)

*Primary Examiner* — Javid A Amini

(57) ABSTRACT

A method and process for providing three dimensional (3-D) virtual image of a patient in metaverse or 3-D hologram for surgical or other procedures, wherein the avatar of a medical practitioner, imitating the actions of the practitioner performing the procedure, can visually identify the organs and the location of the instruments in real-time inside patient. The image data stream generated in real time can be saved in a data base for later re-creation of the image. The re-creation of the image with spatial coordination and updating in time is usable as a review and a teaching/training tool. The implemented Metaverse provides all details collected and combined from the multiple imaging systems. It is usable as a diagnostic tool, a practice tool a teaching tool and real time direction and feedback tool by the medical community for procedures. The real-time image in Metaverse provides critical visual capabilities during procedures.

20 Claims, 2 Drawing Sheets

Figure 1:
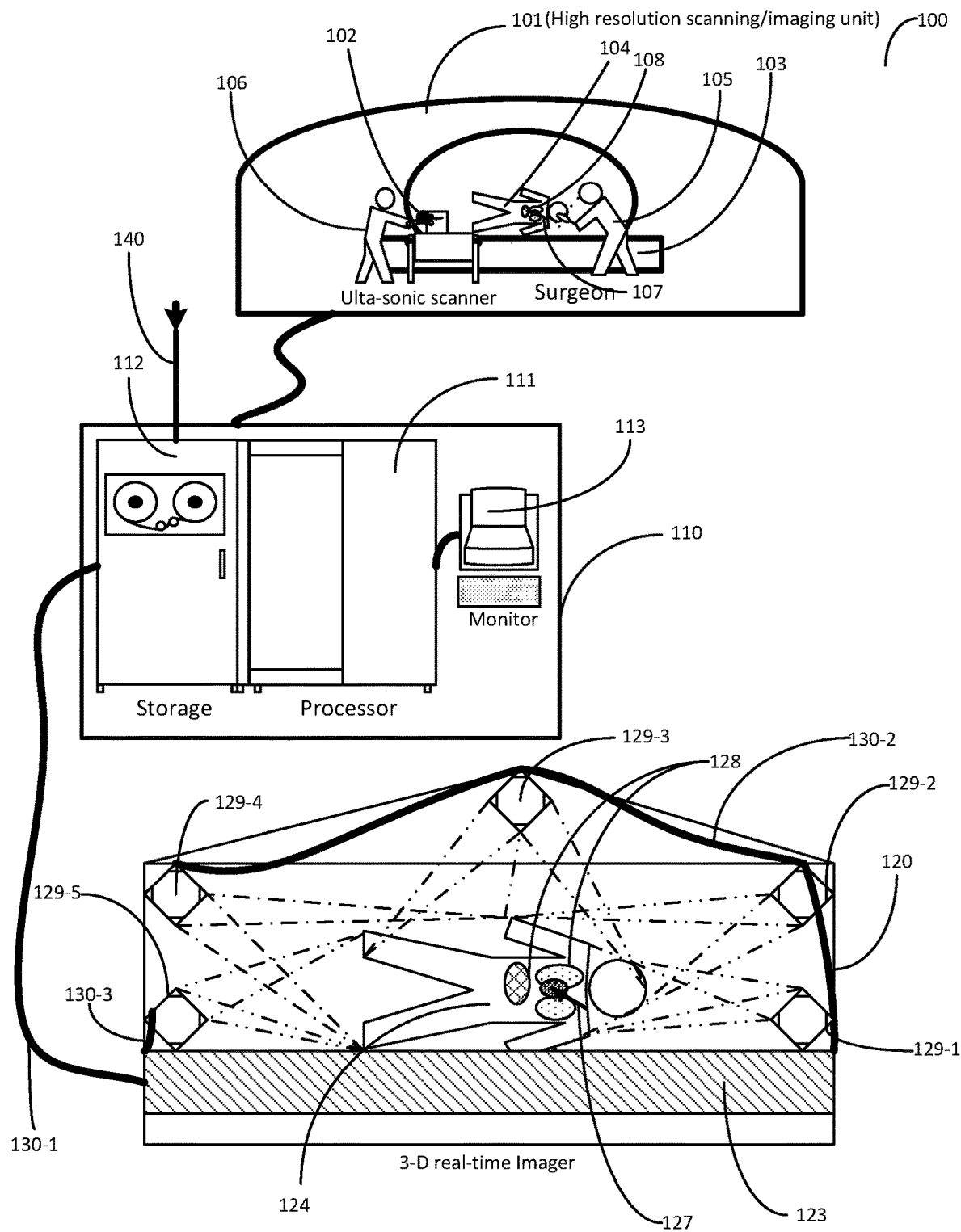

(51) Int. Cl.
    *A61B 34/20*    (2016.01)
    *A61B 34/30*    (2016.01)
    *A61D 1/00*     (2006.01)

(56) References Cited

U.S. PATENT DOCUMENTS

| | | | |
|---|---|---|---|
| 2007/0270680 A1* | 11/2007 | Sheffer | A61B 34/20 600/407 |
| 2019/0380792 A1* | 12/2019 | Poltaretskyi | H04N 13/122 |
| 2020/0085511 A1* | 3/2020 | Oezbek | H04N 13/344 |
| 2022/0179359 A1* | 6/2022 | Pi | G03H 1/2294 |

* cited by examiner

USE OF REAL-TIME AND STORABLE IMAGE DATA STREAM FOR GENERATION OF AN IMMERSIVE VIRTUAL UNIVERSE IN METAVERSE OR A 3-D HOLOGRAM, FOR MEDICAL AND VETERINARY TEACHING AND TRAINING

CROSS REFERENCE TO RELATED APPLICATIONS

This application is a continuation application of pending U.S. application Ser. No. 17/974,538 titled: Use of Immersive Real-time Metaverse and Avatar and 3-D hologram for Medical and Veterinary Applications using Spatially Coordinated Multi-imager based 3-D Imaging filed on 27 Oct. 2022.

FIELD OF INVENTION

This invention addresses the need of the medical and veterinary community to visualize in real time and in multi-dimensions, the field of operation and the location of instruments during procedures and also accurate placement of medicines using a virtual reality metaverse environment. Specifically, the use of such visualization, within a virtual universe of Metaverse or a 3-D holographic image, as a teaching and training tool.

DESCRIPTION OF WHAT IS AVAILABLE AND REASON FOR THE INVENTION

Today most of the robot assisted procedures are conducted by the surgeon operating with a limited vision of the operating field, through microscopes and manipulating the instruments by what is visible in the narrow field of view through the optical cable inserted into the body with the surgical instrumentation. The surgeon has no real wide view of the operating area. There has been scanning and imaging technology such as magnetic resonance imaging (MRI), computed tomography (CT), X-ray, ultra-sound (ultrasonic imaging) etc. which are in widespread use in diagnostic fields. 3-D imaging technology is also available today, to a limited extend using the images generated which are being used for diagnostic and training purposes. This has improved the capabilities existing for practice of nano-surgery and micro-surgery procedure (key-hole procedures) and made them more prevalent. But as of now there are no capabilities for viewing the surgery or procedure in a virtual 3-D image projection where the individual doing the procedure can visually see what is being done in real-time in a simulated virtual environment or as an avatar in a virtual environment such as Metaverse. Such a capability if available will be very useful to improve the efficiency of procedures and reduce the problems substantially for operations and for other invasive, non-invasive, minimally invasive, and key-hole procedures.

The MRI scanning and CT scanning are all techniques used today for diagnostic purposes. These are both high resolution scanning methods. These high-resolution scanning and processing of the scanned data are used to generate usable information and images. But the process of image generation is slow and not real time. The images need to be reconstructed by mathematical computation which makes it a good and reliable diagnostic tool but not easily usable in real-time procedures or consultations during the procedures. As they are not real-time, they are not usable in procedures to see the location of the instruments inside the body as the procedures happen. This makes them not suitable, by themselves, for the applications which are covered by the current invention.

Low intensity X-ray and Ultra-Sonic scanning are two of the currently available other modes of imaging in use for real-time imaging in the medical field. These imaging techniques provide fast image generation and display capability in real-time, but with somewhat lower resolution. All these above mentioned techniques are in use today mainly as stand-alone applications. It will be of use if a system and method can be found that provide real-time visual imaging capability with spatial coordination, such that virtual 3-D images and 3-D holograms can be generated and updated in real-time for conducting procedures with full visibility to the field of the procedure and instrument placement as the procedure is conducted. If such an imaging capability is established, it will also help generate and implement a virtual universe where the medical practitioner can follow his actions in real-time. This is now becoming possible with the advent of virtual reality universe, metaverse, that can be used for such purpose. Such a spatially coordinated virtual 3-D image and 3-D holograms where the medical practitioner or surgeon can be fully immersed in the virtual reality, will also enhance the capability to provide automated robotic implementation of procedures.

What is Needed

A method and process for providing three dimensional (3-D) virtual image of a patient in metaverse for surgical or other procedures, wherein the avatar of a medical practitioner, imitating the actions of the practitioner performing the procedure, can visually identify the organs and the location of the instruments in real-time inside patient. Such an image reconstruction with spatial coordination provides a usable metaverse implementation with the medical professional's persona as avatar, usable as a training and supportive tool in medical applications. It is a very valuable, especially for the medical and surgical community. The implemented Metaverse provides all details collected and combined from the multiple imaging systems. It is usable as a diagnostic tool, a practice tool a teaching tool and real time direction and feedback tool by the medical community for procedures. The real-time image implemented as Metaverse provides critical visual capabilities during procedures.

What is proposed hence is the use of ultra-sonic or low intensity X-ray real-time imaging techniques, that are fast imaging techniques providing real-time imaging capability, used in conjunction with high resolution scanning techniques that provide clear high resolution imaging capabilities, such as MRI or CT, for generation of spatially aligned real-time continuously updating 3-D image data of the patient. The idea is to use this data to generate a 3D virtual image of the patient and the operating environment as a virtual universe, to be presented to the medical practitioner within the metaverse, thereby providing enhanced real-time visual capability for critical procedures. This is a new field of application which the inventors believe is an emerging and highly useful field in medical imaging applications. By making the action of the medical staff and the use of instrumentation within the operating identifiable by embedding the necessary sensor devices in the clothing, gloves, and instruments, it is possible to make the activity within the operating environment visible and followable in real-time in the metaverse. In the metaverse each individual will be represented as his/her avatar and the activity of the individual will be visible as the activity of the avatar enabling full visual control of actions in and around the patient on the operating table with full spatial coordination.

SUMMARY OF INVENTION

The present invention is aimed at providing the medical practitioners of both medical and veterinary community, tools to conduct invasive or minimally invasive procedures with full visibility and control using spatially aligned real-time updated 3-D holographic images within a virtual reality universe, such as immersive virtual reality metaverse platform, in real-time, for guidance of tools and placement of medicines while enabling real-time viewing, direct interaction and follow-up by the surgical team and experts all represented as avatars within the metaverse during the procedure itself. The invention is also an enabler, using metaverse with fully immersive 3-D virtual image and 3-D holograms for improving the diagnosis of problems, planning of procedures, identifying problem areas early, improving the capability to do remote viewing and consultation with experts in the field, thereby reducing the cost and improving success rate of procedures. This invention also provides the capability to practice procedures virtually within the metaverse environment, outside of the patient's body on the 3-D holographic image of the actual individual patient in metaverse, prior to start of procedure, so that the team becomes familiar with the procedure and the nature of the individual's complexities, before starting the procedure, thereby reducing the time taken, reducing risk, and improving success rate for any complex procedure undertaken.

The present invention using immersive metaverse virtual reality is enabled by combining of image data generated by multiple scanning systems/imaging systems, using pre-defined reference points within and around the patient and the location of the procedure as a basis to generate and update and combine real-time image data with previously acquired image data to provide the capability for generating real-time 3-D virtual image or a 3-D holographic image of an object, region or a person within the field of the scans for generating a fully updated real-time metaverse virtual reality environment presented within the virtual reality universe.

Computed Tomography (CT) scan that use either high energy X-rays or Gama rays, and standard X-ray imaging, though much have improved over the past years to provide good images using lower radiation levels, still damage the tissues due to accumulated radiation dosage. They are capable of low distortion images and deeper penetration through bones and underlying tissues to generate the images. Magnetic resonance imaging (MRI) using magnetic resonance scanning techniques are also very accurate and can produce accurate and detailed images of the human body sections. The problem is that such high-resolution scans require long scanning times with mathematical computations that induce time delay. Hence using these scanning techniques by themselves are not feasible to generate and display useful real-time images that can be used to provide the real-time virtual reality images within the metaverse. MRI further limits the use of instruments that are made with certain metals that are magnetic, which also limits its use in many real-time procedures. All these scanning methods are used today for support and verification of diagnosis. 3-D images usable as a basis for virtual reality can be generated from these scans but these scanning and subsequent imaging techniques are not suitable at present for continuous real-time monitoring and display of the field of procedure using immersive metaverse application. (Though in future we can expect the x-ray sensitivity to be increased for detection, making very high-resolution images possible with very low dose X-ray radiation, thereby making x-rays a viable tool for real-time image generation. Time limitations for computation of image from MRIs and CT scans are also expected to change with the increased speed of computing systems enabling computational capabilities for generating fast 3-D images, such as holographic images, in future). Currently, ultra-sound scanning and imaging has poorer image definition but does not cause permanent harm to the tissues due to exposure to harmful radiation and is a good tool to identify soft tissue regions within the body. It also has no limitation on use of metallic tools within its range for procedures. Hence a combination of the initial scanning using any of the high-resolution scanning systems, forming a basis for generation of images in metaverse, with real-time updating of the immersive virtual metaverse display, by ultra-sound (ultra-sonic scanning) or low energy X-ray or similar real-time scanning capability, will provide the best choice for generation of real time 3-D images, for use in virtual reality metaverse and 3-D holograms. At present ultra-sound scanning is the scan of choice for continuous real-time imaging during procedures, as described in at least one embodiment of the invention.

In order, to provide proper alignment between the multiple scanning techniques used for immersive metaverse, a set of accurate alignment points/objects need to be defined in the three dimensions, enclosing the field of interest which will remain constant and enable other references to be generated around the field of the procedure that reference these fixed alignment points and objects. The set of alignment points and objects enable the scan data from different scans to be combined using the references established to eliminate displacement errors when combining and updating 3-D image data that allow the 3-D images to be generated and displayed in virtual reality metaverse or as 3-D holograms. The preference is to have fixed alignment points and objects that do not change shape, as a primary reference. Some of these alignment points and acoustic or X-ray registration points and reference objects can also be defined in or around, the patient within the region of the procedure and these may be setup as primary reference point and if not feasible as secondary reference points which reference the fixed alignment points that are the primary reference for spatial alignment.

Ultra-sonic imaging is a non-invasive technique that can be used to generate the overall image of the field of operation in real-time. This imaging method is very useful in soft tissue areas as indicated earlier. Current advances in ultra-sound or ultra-sonic imaging have included the capability to detect multiple objects (objects within or on surface of other objects, identification of nerves and blood vessels within the body etc. Ultra-sonic imaging technique does not have long term harmful effects that the high power X-ray imaging has, hence it is preferable to use Ultra-sonic imaging or alternately, low power X-ray imaging, where ultra sound is not feasible or sufficient, for continuous real-time updating of display, including 3-D display within metaverse, for real-time monitoring and metaverse image update during procedure, with initial accurate high resolution imaging support from, MRI, CT, high power X-ray or other imaging technologies to develop a complete 3D Imaging basis such as to provide immersive metaverse 3-D images in virtual reality and 3-D holographic images of the field of interest. Such a combination image development with real-time update is what will make the metaverse usable for diagnostic imaging, for procedure planning purposes, as well as for real-time tracking during implementation of invasive or minimally invasive procedures in metaverse virtual reality with the physicians, physician's, assistants, and consultants. Such a capability will also be highly usable in medical procedures using robotics where the procedure can be followed in the metaverse environment using the avatar of the operators or consultants.

To generate the virtual reality universe of metaverse, the image data from these various scans produced are each converted to image data in a standard format that can be combined to produce the combined real time up-dated image data, using processing system, clustered systems or distributed systems having sufficient processing power. The combined image data is then converted to a usable format, usable to produce the virtual image, as display, in immersive metaverse virtual reality, or as 3-D holographic image of the patient showing details of the field of the procedure. The image produced from the data generated and provided within the metaverse virtual reality is continuously updated in real-time using the ultra-sound or low power X-ray scanning result. The standardizing, combining, and processing of the scan data to produce the combined image data to be used in the metaverse is using the processing power of, any one of a dedicated image processing system that is a stand-alone processing system, distributed processing with high bandwidth interconnect in a cluster system, or a fully distributed processing system on the web. The image data produced and updated in real-time is provided to an image generator, such as an image generator for virtual reality immersive metaverse or a set of hologram projection devices that generate the real-time virtual 3-D image using any of the available imaging techniques available. Such generated image is also made useable in the virtual universe of metaverse or 3-D hologram of the patient and the location of the procedure. The real-time image generated and used in the metaverse will provide the capability to view the patient and the field of procedure at differing magnifications, and from different orientations within the metaverse without affecting the spatial co-ordination and linkage established to the patient, to enable complete viewing of the procedure and increase the accuracy of the procedure. The metaverse thereby allows the surgical team and operating tools and equipment that may be further optionally equipped with tracking sensors for improved tracking of their movement in the virtual universe, an immersive virtual view/experience, of the operating field, in real-time, during implementation of the procedure. The optional use of appropriate sensors as indicated above enable improved and more exact tracking and display of the actions, as it happens in the real space, within the virtual universe of metaverse, at times more accurately and exactly than the ultrasound generated real-time image updates. Such a combination hence provides additional accuracy within the metaverse during procedures. During diagnostic and planning/practice stages, the 3-D holographic image or the virtual image in the metaverse can be used as an isolated procedure planning and training entity. But during procedure itself the image is placed in controlled spatial relationship to the patient under sedation for active and real-time observation of the procedure, with guided placement of instrumentation, for the procedure and for feeding/placement of targeted medication, using updates from the continuous monitoring real-time imaging scanners, typically ultra-sonic scanners or low power X-rays placed critically at spatially defined locations and any optional sensors used for tracking the instruments. This allows a complete 3-D view of the field of the procedure with updates in real-time within the metaverse virtual reality during the procedure. Such a capability is expected to be extremely useful for placement of targeted medicines and radio isotopes for cancer and other similar treatments.

The generation and use of the virtual imaging and 3-D holographic imaging capability allows the formation of an image which, in a typical case, may be a 3-D holographic picture, in real-time, to be used in the virtual reality metaverse for complete understanding and planning of the procedure ahead of time using the individual and the field of procedure itself as practice subject. The virtual image of the patient provided within the metaverse will reduce the time the patient has to be worked on and provide for pre-planning of possible complications before the procedure, making for higher safety and faster recovery. The images produced and made available within the metaverse during the procedure itself will be spatially associated with the patient and show the location of the tissues and organs and the location of the instruments in an immersive real-time relationship using the continuously updated display, within the metaverse, for monitoring and accurate execution of the procedure.

It should be noted that even though ultra-sonic scanners are the preferred continuous scanning and updating scanners of choice today, this can change as improvements in other scanner types are made or new combination scanners and sensors are developed, which provide equal or better capabilities for the continuous and real-time monitoring and display. It should also be noted that the improvement in ultra-sonic and other scanning methods and new development of scanning techniques may provide for replacement of currently used scanning/image capturing techniques indicated in this application as being used. Any such improvement/replacement of scanning systems or components of scanning systems are to be expected over time and is covered by the application.

The use of a spatially aligned virtual image, with real-time updating of the instrumentation and activities within the procedure field, enabling virtually immersive metaverse application, provides for improved visibility and accuracy of the procedure, while enabling monitoring and feedback by observing or assisting experts to reduce problems, in real-time, as avatars, during invasive or minimally invasive procedures. The reduced time taken and reduction in problems reduce the risk and trauma to the patient.

Objectives and Advantages of the Disclosure

Some of the clear advantages of the applied concepts are:
1. Possible pre-planning of the procedure in a virtual reality metaverse or using a 3-D holographic environment, on the individual who is being considered for a procedure. The virtual environment of the metaverse or 3D holographic image being generated by combination of multiple imaging techniques.
2. Improved capability for fully immersive diagnostic evaluation with consultation with experts at remote locations, within the metaverse, with full capability to view and study the problem and to suggest improvements to procedures on the individual.
3. Enable pre-implementation practice of the procedure on the available spatially linked within the virtual image in metaverse or using 3-D hologram, to identify and get accustomed to the peculiarities and uniqueness of the individual and the procedure field.
4. Full visibility to the individual, including nerve locations, arteries, and veins in the field of procedure and other organs, allow unique pre-planning and practice of procedure to avoid emergency situations and mistakes.
5. Using continuous imaging for updating of the procedure field providing real-time viewing and monitoring capability within the virtual reality metaverse during procedure to see that there are no problem areas.
6. Better visibility of the field in which the procedure is taking place with specificity of location of the instruments enabled with sensors and robotics used in the procedure field.
7. Capability to have remote procedures directed by experts, without them being present on location, using remote real-time execution monitoring within the immersive virtual metaverse capability.
8. Capability to be present as avatars within the metaverse virtual reality environment/universe and provide advice to the expert conducting the procedure in real-time by observing experts to help overcome difficulties.
9. Ability to ensure nothing un-wanted or foreign is left behind within the surgical area at the end of the procedure.

Explanation/Definition of Terms

1. Scanning system and imaging system are used interchangeably. Typically, they comprise at least an image scanner and at least one image detector that generates the image data from the scan input.
2. 3-D image stands for three dimensional image
3. Virtual reality may require specialized optical devices to be worn for viewing of the 3-D image and immersion in the virtual reality metaverse as avatars.
4. Metaverse is a term that in this application means an immersive 3-D virtual reality universe implemented with or without special visual paraphernalia.
5. Avatar in this application is a representation of an individual in the virtual reality metaverse. Each Avatar within the metaverse is representing an individual.
6. Avatars when implemented in metaverse can be designed to replicate the actions of the individual outside the virtual reality that it represents, within the virtual reality. The accuracy of such action replication on the display may be improved by use of appropriate sensors that enhance the linkage between the individual and his/her avatar.
7. Use of Instruments and equipment if linked to their images can replicate and tack their movement outside the virtual reality, within the virtual reality display. These movements can also be enhanced by use of appropriate sensors embedded within the instruments used.

DRAWING FIGURES

FIG. 1: Is a typical block diagram of a system for the virtual image generation with spatial coordination, for use in the virtual reality immersive metaverse as per an embodiment of the invention.

Figure 2:
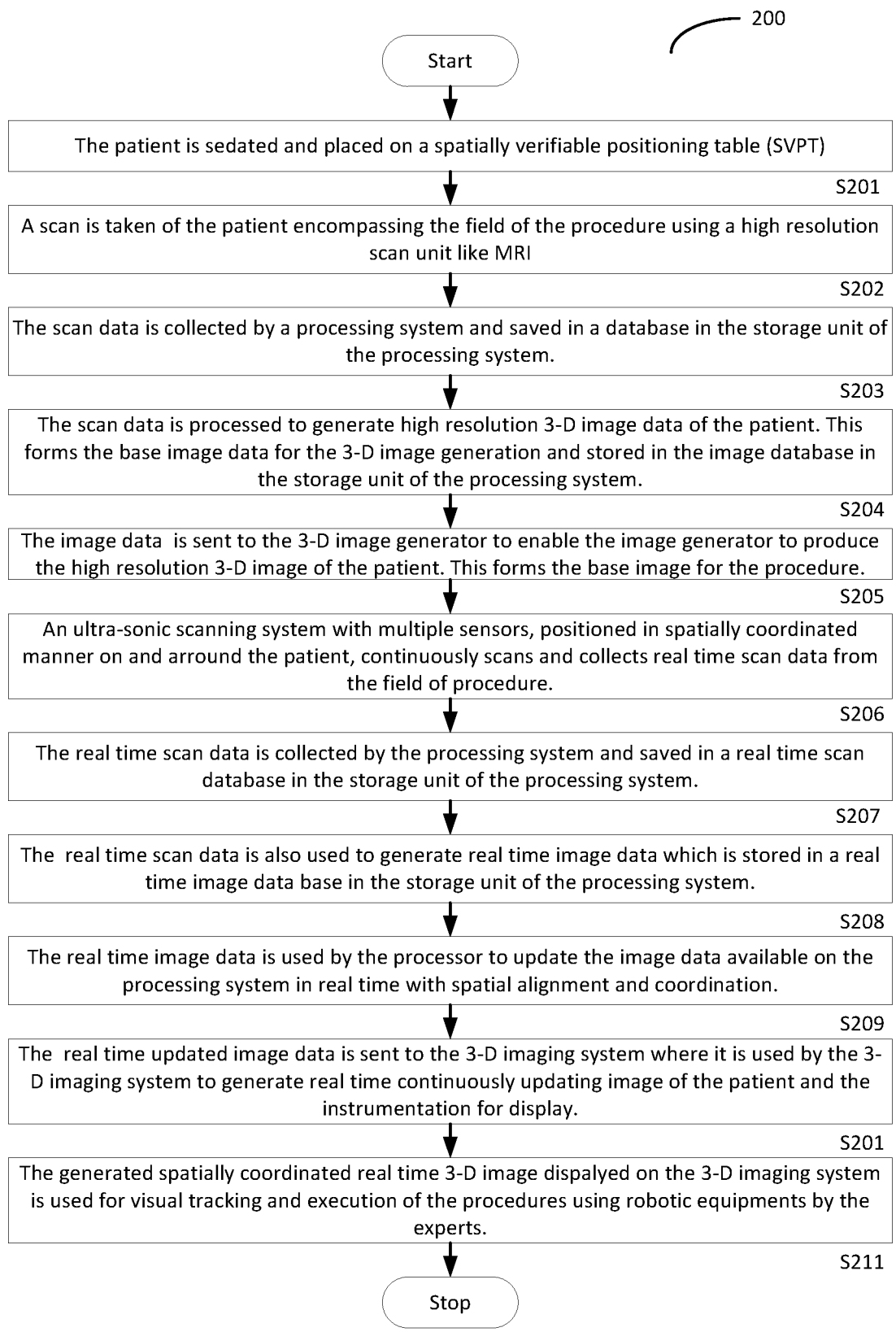

FIG. 2: Is a flow chart of the use of the development of a spatially linked image for use in the metaverse for procedures using immersive avatars within the virtual reality metaverse as per an embodiment of the invention.

DESCRIPTION OF THE INVENTION

A method and process is described for providing Non-Invasive immersive virtual image for use in metaverse applications (e.g. a three dimensional holographic image) of the patient in a spatially coordinated and updatable manner, such that during surgical or other procedures the persons performing the procedure, or acting as advisors can be virtually immersed in the metaverse as his/their own avatars during conduct of the procedure with visual identification of the organs and the location of the instruments in real time inside the body. Hence a spatially aligned non-invasive imaging and reconstruction for fully immersive virtual applications in metaverse or for 3-D holographic image generation using any available image generator, such as a 3-D projector, generating a virtual image of the patient for use in metaverse, will be a very valuable tool to the surgical community. The high-powered computing capabilities, including cluster processing and distributed processing capabilities with high band width interconnection combined with the modern advances in fast imaging virtual imaging techniques, individually or in combination, combined with noise filtering and error correction capabilities, have made accurate virtual imaging for metaverse applications and 3-D holograms from scans a reality. These immersive virtual images (within metaverse) are usable as a diagnostic tool and implementation tool by the medical community. It can also be a valuable teaching tool. There may also be other applications in medical and vet related areas which may emerge as the technology develops and new use cases become apparent to individuals practicing the art.

By using these spatially coordinated, real time, immersive virtual metaverse capabilities and holographic or other available types of image capabilities during surgical or other procedures, with the medical professional performing the procedure immersed in the virtual reality metaverse as avatars, are able to enhance the capabilities provided to the professional to visually identify the organs and the location of the instruments in real-time inside the body of the patient. By replicating the motions of the medical professional, the avatar within the metaverse is able to act in a manner that makes the procedure accessible to the medical professional outside the metaverse. The advances in the scanning techniques, such as X-ray, CT-scans, nuclear medical scans, MRI scans and Ultra-sound scans, individually and in combination with improved noise filtering capabilities enable generation of accurate virtual images for metaverse and 3-D holograms. This has been made easier by the using availability of high-power, high-speed processors, that comprise cluster processors and distributed processors for combining and manipulation of scan data. The medical practitioners/professionals can use these types of images produced and displayed within the immersive metaverse or any of the other available virtual image generators usable for metaverse of 3-D holograms, as diagnostic tools, practice tools and training tools. The images produced and used in immersive virtual metaverse enable the capability for having expert consultants providing second opinions and advice over long distance by participating in and reviewing the procedure in real-time also as avatars for invasive as well as Nano/micro-Surgery, using robotics with visual coverage of the whole area of the surgery, unlike the limited view through a scope available today. This is one of the many areas that benefits most by this invention using metaverse. The real time visual capabilities provided by the immersive metaverse with the procedure and equipment spatially aligned to the patient, enable supervision and guidance of the location of robots in the wider field of the procedure within the body. The total combined view provided by the virtually immersive capability also help to reduce errors during procedure. The immersive virtual metaverse will provide accurate real-time guidance to the instruments used for procedure and placement of medicines within the human body to achieve best results, for applications such as focused radiation therapy. By using enlargement and magnification of the virtual image in metaverse virtual reality, using capabilities provided by the processing units, the metaverse, is able to provide better coverage of the area of the procedure so that the placement and movement of instruments can be more accurately followed than when guiding them when looking through a scope with limited field of view.

The availability of an immersive virtual capability with full 3-D visibility, such as implemented in in a holographic image and metaverse, of the patient, will also help the surgical team practice the operation outside the patient, before starting the procedure, so that there is reduced risk of failure. The diagnostic capability of such a technology will be substantial as experts can directly participate in the operation and understand its ramifications, in real-time, without being present on site and provide feedback to the surgeon/expert performing the procedure during planning stages as well as in real time during the procedure.

By combining high resolution scan data from scanners such as MRI, CT, or X-ray with other suitable high speed real-time scanning techniques, such as ultra-sound, the virtual environment of the metaverse enable the formation of a real-time three dimensional holographic image and immersive virtual metaverse spatially linked to the patient on the table as also the avatars of the medical practitioners within the metaverse. Hence the doctors are able to determine in real-time what is being done and where the instrumentation is and what need to be done further to complete the procedure and where to place medication within the affected regions for maximizing its impact.

DETAILED DESCRIPTION OF INVENTION

FIG. 1 shows an exemplary and non-limiting system 100 for extracting image data for generation of virtual immersive metaverse implementation as per one embodiment of the invention.

The patient under sedation may be located on a spatially verifiable reference generation unit (SVRU), such as a positioning platform or positioning table (SVPT) 103. The SVRU provide fixed and accurate reference points and reference surfaces which allow fixing of additional reference points around the patient and within the field of procedure for convenience and accuracy, referencing these fixed references on the platform. Using these references, the location and position of any items within the field are always referenced and recognized with relation to the reference points fixed including the SVRU such as an SVPT 103. These reference points are used for aligning and combining scan data from multiple scanning systems, such as the high-resolution scans and real-time scans to generate the combined scan data that is used to generate the necessary real-time 3-D image data for the virtual 3-D image used in the metaverse. The reference points are hence used to align the various scans from differing imaging systems used in the generation of the immersive virtual real-time image in metaverse. The scan data from multiple imaging systems are combined effectively and aligned to each other using the references, minimizing the displacement errors that can occur when using data from multiple sources.

A high-resolution imaging unit 101, (also called a high-resolution scanner) such as magnetic resonance imaging (MRI) or Computed Tomography (CT) imaging, is used to generate an accurate and high resolution scan of the patient, 104, (may be limited to the field of the procedure) under sedation. This high-resolution scan data (HRSD) is coordinated spatially with the references provided by the SVPT 103 for providing spatial alignment to any generated images.

A series of ultrasonic scanning heads, that can operate individually or in combination, from an ultra-sonic imager 102, (also called ultra-sonic scanner) are placed at accurately identified coordinate locations on or around the patient with the ultra-sound transmitters and receivers in intimate contact with the patient's body, (not clearly shown in figure for clarity) to provide full coverage of the field of procedure and be also spatially coordinated with the reference points provided by the SVPT 103. The ultra-sonic scanning tech. 106 using the ultra-sonic imager 102 generate continuous scans of the field of the procedure in real time during the procedure being conducted by the doctor/surgeon/medical practitioner 105 on the patient 104. The field of the procedure in FIG. 1 for clarity of example shows the location of organs 108 and instrumentation in place 107 within the field of the procedure which are not directly visible outside the virtual reality metaverse.

The high-resolution imaging unit 101 and ultra-sonic imager 102 as well as the spatially verifiable positioning table (SVPT) 103 are linked to a high-speed data and image processing system (processing system) 110 for collection and storage of the scan data from all imaging systems and sources. The system 110 does the image processing and image data preparation, converting the collected image data to a standard format for combining and generation of the image usable by the immersive virtual metaverse. The processing system 110 may comprise at least one processor 111, a storage unit 112, that has a plurality of image data inputs to collect image data from various imaging systems, at least a program storage and multiple databases with image data storage capabilities, including image data at various stages of process and conversion, and at least an input/output (IO) terminal 113, enabling data and program input and image viewing capabilities. The scan data from the high-resolution imaging unit 101 is collected and stored in a high-resolution scan database and the ultra-sonic scan is collected and stored in a real-time scan database in the data storage unit 112.

The processing system 110 processes the spatially verifiable scan data generated by the high-resolution imaging unit 101 to convert it to image data to a standardized and usable form for generation of the image within the metaverse and/or 3-D holographic image, with spatial coordination. The processing system 110 saves the converted and standardized image data in an image database in the data storage unit 112. The processing system 110 further convert the real-time scan data from the ultra-sonic scanner 102 to the standardized format and use the real-time data combined with the high-resolution image data to generate the immersive virtual image in metaverse and/or the 3-D holographic image. The immersive virtual image in metaverse and the holographic 3-D image is updated in real-time using the real-time ultra-sound data continuously. This enable a reasonably high-resolution image to be displayed in the metaverse consistently. The real-time ultra-sonic data is also spatially coordinated with the patient and high-resolution scan data using the reference points provided by the SVPT 103, enabling the converted ultra-sonic scan updates to be fully coordinated and aligned spatially with the existing scanned image data stored in the processing system 110. This allows the processing system to generate the necessary combined image data enabling continuous updates to the virtual image in the metaverse in real-time. The real time scan data from the ultra-sonic sensors of the ultra-sonic imager, 102, hence enable real time modification of image data and to the immersive virtual image in metaverse and or the 3-D holographic image, as procedures happen.

The real time image data generated by the processor 111 as updates to the 3-D image data are also stored in a real time image database in the data storage 112 and retained for analysis as historic data of the procedure. The real time scan data is converted and used by the processor 111 to update and modify the stored image data on a continuous and real time basis. This updated image data is used for generation of the any 3-D holographic image and the virtual immersive metaverse of the embodiments of the invention.

In addition to the scan data using the multiple scanning systems the virtual universe uses a set of optical and infrared scanners to collect and combine the data surrounding the patient, this data is used to generate and expand the virtual universe surrounding the patient and allow the avatars of individual medical professionals to be present within the metaverse. By use of appropriate sensors attached to the individuals within the procedural environment the movement and actions of the individual medical professionals who are present within the operating environment are made to be replicated by their avatars within the metaverse as described previously. The processing system 110 may be used to combine and process all the data including the visible, infrared and sensor data or a separate processing system may be employed to process the visible, infrared and sensor data from the environment prior to combining it with the scan data available to create the virtual universe of the metaverse.

The processing system 110 is linked to a 3-D image generator 120 such as a holographic projector or holographic image generator, for generating the virtual 3-D image with spatial coordination of the patient, for generation of the metaverse from the combined and up-dated image data produced and manipulated for generation of the 3-D image for implementing the metaverse, by the processor 111. (as described above this may include the scan data and the other environment data used for generation of the virtual universe of metaverse.

The virtual metaverse 3-D imager using the 3-D image generator 120, such as a holographic projector, comprises at least a reference base 123 and multiple projectors 129-1 to 129-5. There is additional processing capability built into the 3-D image generator, 120, for data updating, data distribution and data manipulation. The updated image data generated by the processing system 110 is providable via data links 130-1 to 130-3 to the various projectors and external metaverse generators which working individually or together, depending on the type of imager used, enable the formation and display of the metaverse of virtual 3-D image of the patient 124 within the 3-D metaverse imager 120. The virtual 3-D image of the patient 124 will provide detailed view of the patient 124 with internal organs 128 as generated from the scan data from the high-resolution imaging unit 101 are combined with the real time scan inputs from the ultra-sonic imager 102, with spatial coordination and alignment to generate real time image data enabled to provide the view of the field of the procedure, instruments 127 being used and placement of these instruments with the field where the procedure is undertaken in real time.

The original high resolution scan data from the high-resolution image unit 101 used to generate the initial image data for the 3-D imager 120 are updated using real-time scan inputs from the ultra-sonic scanner 102 by the processing system 110, which combines the inputs in real-time in a spatially coordinated fashion by referencing the coordinates of the SVPT 103 and placement of the ultrasound sensors on the body of the patient. This real-time updated scan data is processed by the processing system 110 to continuously update the 3-D image data and generate real time 3-D image 124 of the patient with the procedure being conducted and the instrumentation used 127 and provide in the metaverse to the doctor/surgeon and to the expert advisors.

By providing a communication capability 140 (either by Wi-Fi or wired) to the processing system 120 it is possible to send the 3-D image data to remote sites by internet or other communication means, for visual following of the procedure by off-site experts, who are then able to provide advice to the doctor 105 conducting the procedure in real time while viewing the procedure in real time. It is also possible to conduct the robotic manipulations over the communication channel by an expert in remote location and hence participate in the procedure if it is necessary.

The embodiments of the invention may be described as an exemplary and non-limiting process, which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a procedure, etc.

FIG. 2 is a flow chart of a spatially linked 3-D hologram and metaverse development in real-time of the patient and the field encompassing the procedure area, for procedures as per an embodiment of the invention.

The patient is sedated and placed on a spatially verifiable stage or positioning table (SVPT) that provides three-dimensional (3-D) reference points around the patient that are referenced by the multiple scanning systems to align the collected scan data and hence eliminate displacement errors that are possible when combining the scans from different scanning systems and scans taken at different times. S201.

One or more scans are taken of the patient encompassing the field of procedure using a high-resolution scan unit such as MRI or CT scan to cover all the details of the patient and the field of the procedure. S202.

The high-resolution scan data are collected by a processing system and saved in a scan data database in the storage unit of the processing system. S203.

The high-resolution scan data is processed by the processing system to convert it to a standardized format suitable for combining with other scan data from other scan systems and to generate high resolution 3-D image data ready for feeding the 3-D image generation system, such as 3-D holographic projectors. The 3-D image data is stored in an image database in the storage unit of the processing system. S204.

The image data is sent to the 3-D image generator to enable the image generator to produce the high resolution 3-D image of the patient. This forms the base image of the patient and the field of procedure for the generation of the initial metaverse or the holographic 3-D image combining with real time image data for use during the procedures. S205.

An ultra-sonic scanning system or a low intensity X-ray system with multiple sensors is used to generate the real-time scan data from which to produce the real-time image data. The transmitting and receiving sensors used for real-time imaging are positioned in spatially coordinated manner, with coordinates identified with respect to the available reference points already existing, on and around the patient. These sensors provide optimal image scans and collect continuous real-time image data from the field of procedure. S206.

The real-time image data is collected by the processing system in real-time and saved in a real-time scan database in the storage unit of the processing system. S207.

The real time scan data collected by the processing system is also converted to the standard format by the processing system, when necessary, and used to generate real-time image data which is also stored in a real-time image data base in the storage unit of the processing system. S208.

The real-time image data is further used by the processor to update the image data available from the high-resolution scans on the processing system in real-time with spatial alignment and coordination using the reference points set up and referenced during high-resolution and ultra-sonic or low level X-ray scanning. The reference points enable the image data from the multiple scans from multiple scanning systems to be integrated in a seamless fashion to produce real time 3-D capable image data of the patient. And the surrounds. S209.

The real-time updated 3-D image data is sent to the 3-D imaging system where it is used by the 3-D imaging system to generate real-time continuously updating image of the patient and the instrumentation that are spatially aligned and coordinated in a verifiable way with the patient for the virtual Universe of the metaverse display and for generation of 3-D holograms when needed. S210.

The generated spatially coordinated real time 3-D image displayed by the 3-D imaging system is also useable for visual tracking and execution of the procedures using robotics and other instruments by the experts. S211.

Embodiments of the invention may be a machine-readable medium having stored thereon instructions which program the processor to perform some, or all of the operations described above. A machine-readable medium may include any mechanism for storing or transmitting information in a form readable by a machine (e.g., a computer), such as Compact Disc Read-Only Memory (CD-ROMs), Read-Only Memory (ROMs), Random Access Memory (RAM), and Erasable Programmable Read-Only Memory (EPROM). In other embodiments, some of these operations might be performed by specific hardware components that contain hardwired logic. Those operations might alternatively be performed by any combination of programmable computer components and fixed hardware circuit components.

While the invention has been described in terms of several embodiments, those of ordinary skill in the art will recognize that the invention is not limited to the embodiments described but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

What is claimed is:

1. A method for generating a real time image data stream for enabling a Real-time visualization in a virtual universe of a metaverse or generating a real-time 3-D holographic image of a field of scan, the field of scan comprising a patient, a surround of the patient, and a location of a procedure, the method comprising: combining with spatial alignment, data on the patient and the surround of the patient collected from sets of optical and infrared scanners with image data generated from scans from multiple diverse types of scanning systems comprising at least a high-resolution scanning system and at least a real time scanning system; wherein the high resolution scan data from the high resolution scanning system is processed by a processor to mathematically reconstruct and output in non-real time, an image data, that is combined with the data from the optical and infrared scanners to output an initial base-line image data of the field of scan, comprising the patient, the surround of the patient, and a field of a procedure, the base-line image data generated with spatial alignment using pre-established alignment points; the at least the real-time scanning system outputting real-time scan data, that is converted in real-time to image data that is combined with up dated real-time image data from the optical and infrared scanners to output a real-time image data to be combined with the base (base-line) image data to update and generate a real-time updated image data stream of the field of scan;
   wherein spatial coordination of the base-line image data and the real-time image data is by using the pre-established reference points as alignment points;
   wherein the real-time updated image data stream that is continuously being updated is used to generate and up-date the virtual universe of the metaverse or the real-time 3-D holographic image of the field of scan; and
   wherein the real-time the updated image data stream that is continuously being updated is stored as a real-time continuously updating image data stream of the field of scan in a data storage for use in teaching and training applications at a later time.

2. The method of claim 1, wherein the pre-established reference points used as alignment points are established within, on and around the field of scan.

3. The method of claim 1, wherein the updated real-time image data stream is used to generate the real-time virtual universe of the metaverse or the real-time 3-D holographic image of the field of scan that is updated continuously; wherein the field of scan comprises the patient, the surrounds of the patient, the location and the field of procedure, and the instruments used in the procedure.

4. The method of claim 1, wherein the base-line image data, the stream of real-time image data from the real time scanning systems and the continuously updating combined image data stream are all stored in the data storage for use in training and teaching of medical professionals.

5. The method of claim 4, wherein the stored image data stream comprising the base-line image data, the stream of real-time image data and the continuously updating combined image data stream are used to re-create the virtual universe of the metaverse or the 3-D holographic image of the field of scan during the procedure, for later review of the procedure done, and for teaching and training purposes.

6. The method of claim 5, wherein the re-creation of the field of scan, comprising the patient, the surrounds of the patient, the location and the field of procedure, and instruments used in the procedure over a period of the procedure, in the virtual universe of metaverse, from the stored continuously updating image data stream generated during the procedure, allow medical professionals, students and teachers to be involved as avatars in the field of scan to observe, study and teach the details of the procedure.

7. A method for generation of a real-time continuously updating image data stream of a field of scan, the method comprising:
   generating high-resolution low noise scan data of the field of scan using one or more high-resolution low noise scanning systems;

wherein the field of scan comprises, a patient, a surround of the patient, a field of procedure comprising a location of a procedure and any instruments used in the procedure;

wherein the field of scan further includes a set of pre-defined reference points for enabling spatial alignment of the image data generated from scans from diverse scanning systems; and wherein image data of the field of scan from the one or more high-resolution scanning systems is generated by processing the scan data over time by a processor to mathematically reconstruct and output a standardized and combinable image data of the field of scan;

combining the image data from the one or more high-resolution scanning systems with image data from the optical and infrared scanners that cover the field of scan with spatial alignment, to generate a base-line image data of the field of scan; generating a real-time scan data of the field of scan using one or more real-time scanning systems;

converting and generating real-time image data, from the scan data generated by the one or more real-time scanning systems and combining them and the real-time image data from the optical and infrared scanners into a real-time image data with spatial alignment;

combining and updating the base-line image data with the real-time image data with spatial alignment to generate a spatially coordinated and continuously updating image data stream of the field of scan in real-time;

wherein the continuously updating image data stream of the field of scan is used to generate and update a virtual universe of the metaverse, or a real-time 3-D holographic image, of the field of scan.

8. The method of claim 7, wherein the spatially coordinated and continuously updated real-time image data stream enable implementation of the virtual universe of metaverse or generation of the real-time 3-D holographic image that is updated in real-time.

9. The method of claim 8, wherein the virtual universe of metaverse or the real-time 3-D holographic image enable the surgeon to use the real-time visual updates to follow and conduct the procedure with full visibility of the field of procedure and any instruments used as the procedure is conducted.

10. An imaging system, the imaging system enabled for generation of a real-time updating image data stream enabled for generation of a real-time updating virtual universe of a metaverse, or a real-time updating 3-D holographic image, of a field of scan comprising a patient, a surround of the patient, a location of a procedure, and a field of procedure, all with spatial alignment using pre-established reference points enabling spatial alignment of the image data stream generated from scans from diverse scanning systems;

the imaging system comprising:
one or more processors;
the diverse scanning systems comprising:
one or more real-time scanners;
one or more optical and infrared scanners; and
at least a high-resolution scanner;
wherein the at least the high-resolution scanner is a scanning system that is enabled to scan the field of scan with spatial alignment and provide it to the processor that is enabled to output in non-real time an image data that is combined with output from the one or more optical and infrared scanners of the field of scan to be used as a base-line image data;

the one or more real-time scanners enabled to generate a real-time scan data convertible to real-time image data of the field of scan comprising the field of procedure with instrumentation and the pre-defined reference points usable for alignment;

the processor enabled to generate a continuously updating image data stream with spatial alignment, combining the base-line image data with the real-time image data;

at least an image processing system comprising an image generator coupled to the processors;

the image processing system enabled to receive the image data stream to output real-time updating 3-D image, the real time updating 3-D holographic image or the real time updating virtual universe in metaverse of the field of scan; and wherein the image data stream is enabled to be saved in a data base for re-creation of the field of scan over time for review of procedure and for teaching and training purposes.

11. The system of claim 10, wherein the base-line image of the field of scan is generated at least by processing a scan data, having a lower noise and a higher resolution than any real time scanning systems, generated by the one or more of the high-resolution scanning systems, by the one or more processors over a period of time to mathematically reconstruct and output;

the base-line image data of the field of scan with spatial alignment using the pre-established reference points for alignment.

12. The system of claim 10, wherein the saved image data stream is retrievable and usable to re-create the virtual universe in metaverse for involvement of medical professionals and students as avatars in the field of scan for review of the procedure and for teaching and training purposes.

13. The system of claim 10, wherein the real-time scanning systems used are enabled to generate scan data convertible in real-time to image data with higher noise, that need to be filtered out, for combining with the base-line image data to generate the image data stream.

14. The at least the image processing system of claim 10, wherein the at least the image processing system is communicably connected to the internet for sending the real-time image data stream to experts at remote sites enabling them to generate the real time updating virtual universe in metaverse or the real time updating 3-D holographic image of the procedure in real-time for monitoring and providing advice to the individual conducting the procedure and further participate in the procedure in real-time.

15. The metaverse of claim 10, where in individuals conducting the procedure and consultants are enabled to be present as their avatars for providing advice, and students are enabled to be present as avatars for following the procedure in real-time for learning.

16. The system of claim 10, wherein the system is configured to enable any one or more of: a training procedure, a pre-planning of procedure on individual patient, a tracking of procedure on the patient in real-time, a review of a completed procedure, a teaching of the procedure.

17. The system of claim 10, wherein the use of additional optical and infrared imaging systems covering the area surrounding the procedure are enabled to enhance the generated real time updating virtual universe of metaverse.

18. A system for generation of a continuously updating image data stream for generation of a virtual universe in metaverse, or a 3-D holographic image, of a field of scan, the system comprising:
- one or more high-resolution non-real time scanning systems enabled for generation of scan data of the field of scan with pre-established reference points in and around the field of scan enabled for providing spatial alignment;
- one or more processors enabled for processing the scan data from the one or more high-resolution scanning systems over a period of time and mathematically reconstruct and output an image data of the field of scan in a standardized format;
- one or more sets of optical and infrared scanners generating image data of the field of scan;
- combining the mathematically reconstructed image data with image data from the optical and infrared scanners to output a base-line image data of the field of scan with spatial alignment;
- one or more real-time scanning system to generate a real-time scan data of the field of scan with the pre-established reference points in and around the field of scan enabled for providing spatial alignment;
- the one or more processors enabled to standardize and convert the real-time scan data to real-time image data in the standardized format;
- the one or more processors further enabled to combine the base-line image data with the real time image data, with spatial alignment to generate an image data stream that is a continuously updating image data stream of the field of scan in real-time;
- the base-line image data, the real time image data and the continuously updating image data stream, all, enabled to be stored in an image database for retrieval, re-creation, and review at a later date; and
- an image processing system enabled to use the image data stream to generate and output a 3-D holographic image or a virtual universe in metaverse of the field of scan;
- wherein the field of scan comprise a patient, a surround of the patient, a location of procedure, medical professionals in the surround of the patient, and instruments used in the procedure.

19. The system of claim 18, wherein the image data stream enables generation of the real-time 3-D holographic image or the virtual universe in metaverse of the field of scan enabled for real-time teaching and training of the procedure.

20. The system of claim 18, wherein the saved image data stream is used later in time to produce the 3-D holographic image or the virtual universe in metaverse of the field of scan, that updates over time showing the procedure, providing a capability for review, teaching, and training of the procedure conducted.

* * * * *